United States Patent [19]
Fujii et al.

[11] Patent Number: 6,011,071
[45] Date of Patent: Jan. 4, 2000

[54] ETHER COMPOUND AND PROCESS FOR PRODUCING THE SAME

[75] Inventors: Yasuyuki Fujii; Hisakazu Furugaki; Katsumi Kita, all of Wakayama; Hideharu Morimoto, Tokyo; Mitsuru Uno, Wakayama; Yasushi Kajihara, Tokyo, all of Japan

[73] Assignee: Kao Corporation, Tokyo, Japan

[21] Appl. No.: 08/952,075

[22] PCT Filed: May 17, 1996

[86] PCT No.: PCT/JP96/01315

§ 371 Date: Nov. 17, 1997

§ 102(e) Date: Nov. 17, 1997

[87] PCT Pub. No.: WO96/36583

PCT Pub. Date: Nov. 21, 1996

[30] Foreign Application Priority Data

| May 17, 1995 | [JP] | Japan | 7-118309 |
| May 29, 1995 | [JP] | Japan | 7-130253 |
| Jul. 18, 1995 | [JP] | Japan | 7-181439 |
| Nov. 2, 1995 | [JP] | Japan | 7-285717 |

[51] Int. Cl.[7] ............................. A61K 31/08; C07C 43/11
[52] U.S. Cl. .................. 514/723; 568/613; 568/618; 568/670; 568/672; 424/78.03
[58] Field of Search .................... 568/613, 616, 568/617, 618, 619, 670, 672, 687, 689, 690, 695, 697; 424/59, 65, 76.1, 78.03; 514/722, 723

[56] References Cited

U.S. PATENT DOCUMENTS

| 2,973,388 | 2/1961 | Riemschneider | 260/615 |
| 4,009,254 | 2/1977 | Renold | 424/59 |
| 4,151,205 | 4/1979 | Cohen et al. | 260/590 R |

FOREIGN PATENT DOCUMENTS

| 0 586 234 | 3/1994 | European Pat. Off. |
| 41 24 199 | 1/1993 | Germany . |
| 48-5941 | 1/1973 | Japan . |
| 48-33037 | 5/1973 | Japan . |
| 63-122612 | 5/1988 | Japan . |
| 6-507654 | 9/1994 | Japan . |

OTHER PUBLICATIONS

Vol. 36, No.24, pp. 4235–4236, 1995 An Alternative Catalytic Method to the Williamson's Synthesis of Ethers Valerie Bethmont, et al.

Chemical Abstracts, vol. 79, No. 10, 1973.

Chemical Abstracts, vol. 79, No. 16, 1973.

*Primary Examiner*—Shailendra Kumar
*Assistant Examiner*—Sreeni Padmanabhan
*Attorney, Agent, or Firm*—Oblon, Spivak, McClelland, Maier & Neustadt, P.C.

[57] ABSTRACT

To provide a novel ether compound which is useful such as an oil agent and a surfactant having the formula (I): $R^1—O—(AO)_n—R^2$, wherein $R^1$ is an alpha-branched alkyl group or an alkyl group having two or more branched chains or a cycloalkyl having 5 to 7 carbon atoms, $R^2$ is an alkyl or alkenyl each being either branched or straight, each having 10 to 30 carbon atoms, A is an alkylene having 2 to 12 carbon atoms, n is a number from 0 to 30, A's being same as or different from one another.

14 Claims, No Drawings

ETHER COMPOUND AND PROCESS FOR PRODUCING THE SAME

This is the U.S. National Stage Application of PCT/JP96/01315 filed May 17, 1996.

BACKGROUND OF THE INVENTION

1. Field of the Invention

The present invention relates to a novel ether compound and process for producing the same. More specifically, the invention relates to a novel ether compound and process for producing the same, which can be used widely as oil for such as cosmetics, detergents and lubricants being colorless, odorless, free from change or development of color and odor with the elapse of time, having little oily feeling, excellent touch, pertinently low viscosity and no irritating effect to eyes. It can also be used widely for surfactants for penetrating agents, emulsifiers, solubilizing agents, dispersing agents, and detergents, having pertinently low viscosity and little stickiness.

2. Prior Arts and Problem to be solved by the Invention

Conventionally, known liquid oils widely used for cosmetics, detergent compositions and lubricants include oils and fats and hydrocarbons obtained from animals, plants or chemical syntheses.

Ideal properties for these liquid oils of general purpose include:

(1) Odorless and colorless;
(2) Free from change or development of color and odor with the elapse of time;
(3) Excellent in touch; and
(4) Pertinently low viscosity.

However, oils and fats are undesirable in the respects of hydrolysis when contacted with water and oily feeling, and hydrocarbons are not satisfactory because of high viscosity in spite of their excellent stability. Thus, all the ideal properties mentioned above have not been satisfied by the known oils.

Conventionally, oils and fats and hydrocarbons mentioned above as well as esters are used as liquid oils for make-up cosmetics removing agents. However, these oils have not satisfied the ideal properties which are required for make-up cosmetic removing agents, that is, being excellent in touch (little oily feeling), easy to remove make-up cosmetics and free from irritation to eyes.

On the other hand, some ether compounds have been known as the oils for cosmetics. For example, JP-A-48-5941 discloses a saturated monoether compound having 24 or more carbon atoms and a side chain at the beta-position; JP-A-48-33037 discloses a higher linear ether compound having 20 or more carbon atoms; JP-A-63-122612 corresponding to U.S. Pat. No. 4,919,923 and JP-A-6-507654 each discloses an ether compound in which one of the alkyl group of the monoether has 6 to 22 carbon atoms; and U.S. Pat. No. 4,009,254 discloses an ether compound in which one of the alkyl group has 1 to 3 carbon atoms and the other alkyl group has 8 to 20 carbon atoms. These ether compounds, however, do not satisfy all the requirements, mentioned above, make-up cosmetics removing agents.

Additionally, in the prior art, surfactants used for such as penetrating agents, emulsifiers, solubilizing agents, dispersing agennts, and detergents have been classified into types of anioinic, catioinic, amphoteric, and nonionic. Among them, anioinic, catioinic, and amphoteric surfactants have electric charge, hence, they are disadvantageous in higher viscosity or stronger hygroscopicity. Nonionic surfactants also have the problems associated with higher viscosity or stronger hygroscopicity since most nonionic surfactants contains hydroxyl groups partially or wholly. Although, some nonionic surfactants do not contain hydroxyl group, almost thereof cannot be used since they predominantly contain ester bonds to be hydrolyzed in acidic or alkaline conditions.

Therefore, an object of, the present invention is to solve the above problems and to provide a novel ether compound which can be used widely as oils for cosmetics, detergents and lubricants, or for surfactants such as penetrating agents, emulsifiers, solubilizers, dispersing agents and detergents. Particularly, an object of the present invention is to provide a novel ether compound being useful as make-up cosmetics removing agents which has little oily feeling, and exhibits high detergency to solid soil such as solid fats and polymers; is excellent in touch when applied to skins; and is little irritate to eyes and easy in formulation.

Means for Solving the Problem

Under such circumstances, the present inventors have found a novel ether compound that can solve the problems mentioned above as a result of intensive studies.

The present invention provides an ether compound having the formula (I):

$$R^1-O-(AO)_n-R^2 \qquad (I)$$

[wherein $R^1$ is an alpha-branched alkyl group or an alkyl group having two or more branched chains or a cycloalkyl group having 5 to 7 carbon atoms, $R^2$ is an alkyl or alkenyl group each being either branched or straight, each having 1 to 30 carbon atoms, and A is an alkylene group having 2 to 12 carbon atoms, and n is a number from 0 to 30, the plurarlity of A being the same or different from one another.]

The present invention also provides a process for producing the ether compound having the formula (I), which comprises reacting a carbonyl compound, represented by the following formula (III):

(III)

[wherein $R^3$ and $R^4$ are the same or different from each other satisfying that

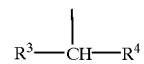

is $R^1$], with a hydroxy compound represented by the following formula (IV):

$$HO-(AO)_n-R^2 \qquad (IV)$$

[wherein $R^2$, n and A are the same as defined in the above], in hydrogen gas atmosphere in the presence of a palladium catalyst supported on carbon powder.

Furthermore, the present invention provides a make-up cosmetics removing agent composition which comprises the ether compound of the formula (I).

Still furthermore, the present invention provides use of the ether compound of the formula (I) to remove make-up cosmetics thereby.

Embodiments of the Invention

Embodiments of the present invention will now be explained in details.

Examples of the alpha-branched alkyl group designated as $R^1$ in the ether compound represented by the formula (I) include $CH_3$—$CH(CH_3)$—$CH_2$—$CH(CH_3)$—, $CH_3$—$CH(CH_3)$—, $CH_3$—$CH_2$—$CH(CH_3)$—, $CH_3$—$CH(CH_3)$—$CH_2$—$CH\{CH_2$—$CH(CH_3)_2\}$—, and $CH_3CH_2CH_2CH_2CH_2CH_2CH(CH_3)$—.

Examples of the alkyl group having two or more branched chains include $CH_3$—$CH(CH_3)$—$CH_2$—$CH(CH_3)$—, $CH_3$—$CH(CH_3)$—$CH_2$—$CH\{CH_2$—$CH(CH_3)_2\}$— and $CH_3$—$CH(CH_3)CH_2CH_2CH_2CH(CH_3)CH_2CH_2$—.

Examples of the cycloalkyl group having 5 to 7 carbon atoms which may have substituent groups include cyclopentyl group, cyclohexyl group, and cycloheptyl group. Furthermore, examples of such substituent groups include alkyl groups having 1 to 3 carbon atoms.

Examples of the alkyl or alkeny group designated as $R^2$, each being either branched or straight and having 1 to 30 carbon atoms, include groups such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, docosyl, triacontyl, oleyl, methylpropyl, methylbutyl, methylpentyl, methylhexyl, methylheptyl, ethylhexyl, hexyldecyl, and octyldecyl; and mixed alkyl groups derived from coconut oil and beef tallow. Among them, straight or branched alkyl groups having 10 to 30 carbon atoms are preferable, further, stgraight ones are more preferable.

Examples of the alkylene group designated as A having 2 to 12 carbon atoms include groups of ethylene, propylene, butylene, pentylene, hexylene, heptylene, octylene, nonylene, decylene, undecylene, dodecylene, 2-methylpropylene, 2,2'-dimethylpropylene and 3-metylpentylene; preferable example is ethylene group.

n is a number from 0 to 30, preferablly, from 0 to 20, particularly preferable 0.

Among the examples of the ether compound represented by the general formula (I) in the present invention, compounds represented by the following general formulae (V), (VI) or (VII) are cited:

   (V)

[wherein $R^6$ represents a group selected from $CH_3$—$CH(CH_3)$—$CH_2CH(CH_3)$—, $CH_3$—$CH(CH_3)$— and $CH_3$—$CH_2$—$CH(CH_3)$—; $R^7$ represents a straight or branched alkyl group having 1 to 30 carbon atoms; E represents an ethylene group; and n is the same as defined above];

   (VI)

[where $R^8$ represents a cycloalkyl group having 5 to 7 carbon atoms which may contain substituent groups; $R^9$ represents a straight or branched alkyl or alkenyl group having 1 to 30 carbon atoms; and E and n are the same as defined above];

   (VII)

[where, $R^{10}$ represents a group selected from $CH_3$—$CH(CH_3)$—$CH_2$—$CH(CH_3)$—, $CH_3$—$CH(CH_3)$—, $CH_3$—$CH_2$—$CH(CH_3)$—, $CH_3CH(CH_3)$ $CH_2CH_2CH_2CH(CH_3)$ $CH_2CH_2$—, $CH_3CH(CH_3)CH_2CH\{CH_2CH(CH_3)_2\}$—, and $CH_3CH_2CH_2CH_2CH_2CH_2CH(CH_3)$—; $R^{11}$ represents a straight or branched alkyl or alkenyl group, preferably a straight or branched alkyl group, more preferably a straight alkyl group, having 1 to 30, preferably 4 to 30, more preferably 10 to 30, carboy atoms; A' represents an alkylene group having carbon atoms 2 to 3, preferably 2, the number of m of A' may be the same or different; and m represents the average adduct molar number of an alkylene oxide being in a range from 1 to 30, preferably, 1 to 20].

In the ether compound represented by the general formula (IV), the sum total number of carbon atoms of $R^6$ and $R^7$ is preferably from 16 to 28.

Suitable examples of the ether compound represented by the general formula (IV) shown above include compounds represented by the following general formula (II), (III) or (IX); a compound represented by the following general formula (II) is preferable in particular for an oil solution of make-up cosmetics removing agent.

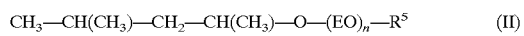   (II)

[wherein $R^5$ represents a straight or branched alkyl group having 10 to 22, preferably 12 to 18, carbon atoms; and E and n are the same as defined above.]

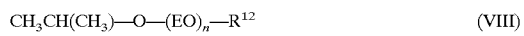   (VIII)

[wherein $R^{12}$ represents a straight or branched alkyl group having 16 to 25, preferably 16 to 20, carbon atoms; and E and n are the same as defined above].

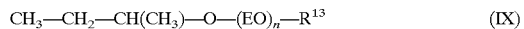   (IX)

[wherein $R^{13}$ represents a straight or branched alkyl group having 13 to 24, preferably 14 to 20, carbon atoms; and E and n are the same as defined above].

Examples of the straight or branched alkyl group having 10 to 22 carbon atoms represented by $R^5$ in the general formula (II) include groups of decyl, undecyl, dodecyl, tridecyl, tetradecyl, pentadecyl, hexadecyl, heptadecyl, octadecyl, nonadecyl, eicosyl, and docosyl, and mixed alkyl groups derived from coconut oil, beef tallow and the like. Among them, straight alkyl groups are preferable in view of obtainable pertinent viscosity.

Examples of the straight or branched alkyl group having 16 to 25 carbon atoms represented by $R^{12}$ in the general formula (VIII) include groups of hexadecyl, heptadecyl, octadecyl, nonadecyl, eicosyl, behenyl, docosyl and tetracosyl, and mixed alkyl groups derived from coconut oil, beef tallow and the like. Among them, straight alkyl groups are preferable in view of obtainable pertinent viscosity.

Examples of the straight or branched alkyl group having 13 to 24 carbon atoms represented by $R^{13}$ in the general formula (IX) include groups of tridecyl, tetradecyl, pentadecyl, hexadecyl, heptadecyl, octadecyl, nonadecyl, eicosyl, behenyl, docosyl and tetracosyl, and mixed alkyl groups derived from coconut oil, beef tallow and the like. Among them, straight alkyl groups are preferable in view of obtainable pertinent viscosity.

Among the compounds expressed by the general formulae (II), (VIII) or (IX), the compounds in which n is 0 are preferable in particular.

As applicable synthesis method for ether compounds represented by the general formula (I), methods for synthesizing a lower alkyl ether, for examples; Williamson synthesis wherein an alkyl halide and metal alkoxide are reacted; a synthesis method wherein an alcohol and a carbonyl compound such as a ketone are reacted in hydrogen atmosphere and in the presence of a catalyst; a synthesis method by an addition reaction of an alcohol with an olefin in the presence of a catalyst; or a synthesis method by a reduction of an ester compound; are cited. Synthesis methods used in the present invention are not limited by the above.

Concretely, examples for process for producing an ether compound represented by the general formula (I) or (XII) include: reacting, as shown by the following Reaction Formula 1, a metal alkoxide represented by the formula (X) with a compound represented by the formula (XI); and reacting, as shown by the following Reaction Formula 2, a carbonyl compound represented by the formula (III) with a hydroxy compound represented by the formula (IV) in hydrogen atmosphere and in the presence of a catalyst.

Reaction Formula 1

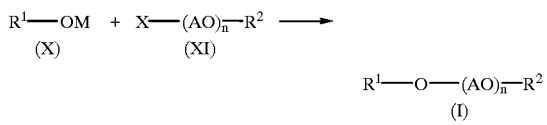

Reaction Formula 2

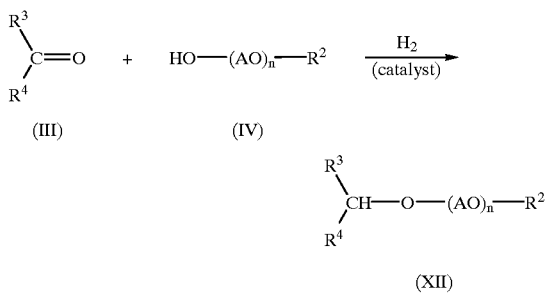

[wherein $R^1$, $R^2$, $R^3$, $R^4$, A, and n are the same as defined above; M represents an alkaline metal; X represents a halogen atom; and

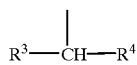

corresponds to $R^1$].

Examples of the metal alkoxide represented by the formula (X) in the Reaction Formula 1 (hereinafter abbreviated as metal alkoxide (X)) include metal alkoxides of sodium, lithium or potassium with an alcohol such as 4-methyl-2-pentanol, 2-butanol, isopropanol, 3,7-dimethyloctanol, 2,6-dimethyl-4-heptanol, 2-octanol and cyclohexyl alcohol. Examples of the compound represented by the formula (XI) (hereinafter abbreviated as compound (XI)) include dodecyl bromide, tetradecyl bromide, hexadecyl bromide and octadecyl bromide.

Instead of reacting the metal alkoxide (X) with the compound (XI) in the Reaction Equation 1; the ether compound represented by the general formula (I) can be obtained by reacting an alcohol such as 4-methyl-2-pentanol, 2-butanol, isopropanol, 3,7-dimethyloctanol, 2,6-dimethyl-4-heptanol, and 2-octanol with the compound (XI) in the presence of an alkali such as particulate sodium hydroxide, particulate potassium hydroxide or 20 to 50% by weight of sodium hydroxide aqueous solution. The reaction molar ratio of the metal alkoxide (X) to compound (XI); (X):(XI) is preferably 1:1 to 1:10. The reaction temperature is preferably in a range of 50 to 150° C., and the reaction time is preferably in a range of 5 to 20 hours. A correlation transfer catalyst such as tetrabutylammonium may also be added thereto.

In the Reaction Formula 2 above, conventional hydrogenation catalysts such as palladium catalyst which is properly supported on a carrier such as carbon, aluminum silicate, zeolite, alumina and silica; or palladium compounds such as palladium hydroxide or palladium oxide can be used. Among these, palladium catalyst supported on carbon powder is most preferably used in the reaction of the carbonyl compound represented by the formula (III) with the hydroxy compound represented by the formula (IV) in a hydrogen atmosphere, since the ether compound can readily and cheaply produced on an industrial scale at a very high yield thereby.

In the present invention, 2 to 10% by weight of the catalyst, based on a carrier such as carbon, is usually supported thereon and applied, though the catalyst can also be used without being supported on a carrier. Or the catalyst may contain 20 to 60% by weight of water.

5% by weight, based on a carrier, of the catalyst supported on a carrier is preferably used in the amount of 0.1 to 10% by weight to the amount of hydroxy compound (IV) to be used. When it is less than 0.1% by weight, the reaction is unfavorably slow even which proceeds. When it exceeds 10% by weight, the reaction is fast, but a side reaction also proceeds. The preferable amount of the catalyst to be used in a range of 0.5 to 5% by weight.

The catalyst can be used in the whole pH region. The catalyst is preferably used in the range of 1 to 8, more preferably 3 to 8 in order to give an optimum reaction rate. The pH of the catalyst is defined here as pH of the solution wherein 2 g of the catalyst powder dispersed into 30 g of deionized water.

Commercial palladium catalyst, especially having a pH thereof in a range of 1 to 8, can be used without any treatment. Even when a catalyst has a pH exceeding 8, it can also be used with adjusting pH thereof in the range of 1 to 8 by washing with water to eliminate alkali portion or neutralizing with acid. The pH of the catalyst can also be adjusted by, for example, the following methods (a) or (b) in which palladium is supported on powdery or granules carbon:

(a) A predetermined amount of active carbon is added to an aqueous solution, containing hydrochloric acid, of palladium chloride or palladium nitrate; water and hydrochloric acid are eliminated under vacuum; and the mixture is dried and calcined in air.

(b) A predetermined amount of active carbon is added to an aqueous solution, containing hydrochloric acid, of palladium chloride or palladium nitrate; water and hydrochloric acid are eliminated under vacuum; and the mixture is reduced in hydrogen atmosphere.

In more details, the predetermined amount of palladium chloride or palladium nitrate and a small amount of concentrated or diluted hydrochloric acid are dissolved in water, and active carbon is added thereto. The mixture is sufficiently stirred and heated under vacuum of 1 to 200 torr, and further, dried at 50 to 150° C., thereby to obtain precursor of palladium chloride catalyst supported on active carbon. The palladium chloride catalyst supported on active carbon is obtained with a treatment of (1) drying and baking in air for 1 to 5 hours at the temperature of 200 to 400° C.; or (2) reducing in hydrogen atmosphere for 1 to 5 hours at the temperature of 80 to 300° C.

As carbonyl compounds represented by the formula (III) used in the Reaction Formula 2, ketone compounds such as acetone, methyl ethyl ketone, methyl isobutyl ketone (4-methyl-2-pentanone), diisobutyl ketone, 2-octanone, methyl heptenone, cyclohexanone, 2-methylcyclohexanone, cyclopentanone; and aldehyde compounds such as citronellal; are cited.

As hydroxy compounds represented by the formula (IX), saturated linear alcohols such as methyl alcohol, ethyl alcohol, propyl alcohol, n-butyl alcohol, n-pentyl alcohol, n-hexyl alcohol, n-heptyl alcohol, n-octyl alcohol, n-nonyl alcohol, n-decyl alcohol, n-undecyl alcohol, n-dodecyl alcohol, n-tridecyl alcohol, n-tetradecyl alcohol, n-pentadecyl alcohol, n-hexadecyl alcohol, n-octadecyl alcohol, and n-eicosyl alcohol; saturated branched alcohols such as isopropyl alcohol, isobutyl alcohol, 2-ethylhexyl alcohol, 2-hexyldecyl alcohol, 2-heptylundecyl alcohol, 2-octyldodecyl alcohol, 2-decyltetradecyl alcohol, and 2-(1,3,3-trimethylbutyl)-5,7,7-trimethyloctyl alcohol; saturated branched alcohols, such as methyl-branched isostearyl alcohols represented by the following formula:

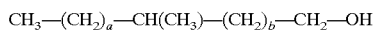
$$CH_3-(CH_2)_a-CH(CH_3)-(CH_2)_b-CH_2-OH$$

[wherein a+b=14, and which having the distribution having the peak of a=b=7]; alkenyl alcohols such as 9-octadecenyl alcohol, farnesyl alcohol, abietyl alcohol; alkenyl alcohols such as oleyl alcohol; monoethers of ethylene glycol such as ethylene glycol monomethyl ether (methyl cellosolve), ethylene glycol monoethyl ether (ethyl cellosolve), ethylene glycol monoisopropyl ether (isopropyl cellosolve), ethylene glycol monobutyl ether (butyl cellosolve), ethylene glycol monoisoamyl ether, ethylene glycol monohexyl ether, ethylene glycol monodecyl ether, ethylene glycol monododecyl ether, ethylene glycol monohexadecyl ether, ethylene glycol monooctadecyl ether, ethylene glycol monoeicosyl ether; monoethers of diethylene glycol such as diethylene glycol monomethyl ether (methyl carbitol), diethylene glycol monoethyl ether (ethyl carbitol), diethylene glycol monoisopropyl ether (isopropyl carbitol), diethylene glycol monobutyl ether (butyl carbitol), diethylene glycol monodecyl ether, diethylene glycol monododecyl ether, and diethylene glycol monooctadecyl ether; monoethers of triethylene glycol such as triethylene glycol monomethyl ether, triethylene glycol monoethyl ether, triethylene glycol monohexyl ether, triethylene glycol monodecyl ether, triethylene glycol monododecyl ether, triethylene glycol monotetradecyl ether and triethylene glycol monooctadecyl ether; monoethers of propylene glycol such as propylene glycol monomethyl ether, propylene glycol monoethyl ether, propylene glycol monoisopropyl ether, propylene glycol monobutyl ether, propylene glycol monoisoamyl ether, propylene glycol monohexyl ether, propylene glycol monodecyl ether, propylene glycol monododecyl ether, propylene glycol monohexadecyl ether, propylene glycol monooctadecyl ether, and propylene glycol monoeicosyl ether; monoethers of dipropylene glycol such as dipropylene glycol monomethyl ether, dipropylene glycol monoethyl ether, dipropylene glycol monoisopropyl ether, dipropylene glycol monobutyl ether, dipropylene glycol monodecyl ether, dipropylene glycol monododecyl ether, and dipropylene glycol monooctadecyl ether; monoethers of tripropylene glycol such as tripropylene glycol monomethyl ether, tripropylene glycol monoethyl ether, tripropylene glycol monohexyl ether, tripropylene glycol monodecyl ether, tripropylene glycol monododecyl ether, tripropylene glycol monotetradecyl ether and tripropylene glycol monooctadecyl ether; monoethers of an alkylene glycol such as 1,4-butanediol monohexyl ether, 2-methyl-1,3-propanediol monooctyl ether, 1,6-pentanediol monohexyl ether, 2,2'-dimethylpropanediol monooctyl ether and 3-methyl-1,5-pentanediol monohexyl ether; and adduct compounds of alcohols mentioned above with ethylene oxide, propylene oxide, or butylene oxide are cited, however, it is not limited by the above examples.

The molar ratio of carbonyl-compound (III):hydroxy-compound (IV) is preferably 1:1 to 20:1, more preferably 1:1 to 5:1. The reaction is carried out in hydrogen atmosphere preferably at 1 to 250 kg/cm², more preferably at 1 to 150 kg/cm² in view of an optimum reaction rate and a minimum extent of carbonyl groups to be reduced. The reaction temperature is preferably in a range of 10 to 200° C., more preferably 50 to 180° C. The reaction time is preferably from 3 to 25 hours, more preferably from 3 to 15 hours.

This reaction can be carried out either without using a solvent or with diluting by an appropreate solvent.

Examples of the solvents that can be used in the reaction include hydrocarbon system solvents such as n-pentane, n-hexane, n-heptane, n-octane, n-decane and petroleum ether; inert organic solvents including ether system solvents such as n-butyl ether and n-hexyl ether. However, it is not limited by the above.

In the make-up cosmetics removing agent of the present invention, though the blending amount of the ether compound represented by the formula (I) is not limited, it is preferably in a range of 6 to 95% by weight (hereafter simply expressed as %), more preferably 10 to 90%, and most preferably 10 to 80%, for both improved detergency and easiness of preparation. The make-up cosmetics removing agent composition of the present invention may further contain, in addition to the ether compound and to the extent not to harm the effect of the present invention, ordinary cosmetics components such as surfactants, oil solutions (extenders), solvents, gelling agents, drug efficacy ingredients, water-swelling clays, polymers, pigments, antiseptics, viscosity regulators, antioxidants, perfumes, and water.

In more details, examples of the anionic surfactants usable in the present invention include sulfates or sulfonates such as alkylsulfates, polyoxyethylene alkylsulfates, sulfosuccinates, taurates, isethionates, and alpha-olefin sulfonates; carboxylates such as fatty acid soaps, ether carboxylates; acylated amino-acids; and phosphates such as alkylphosphate esters. Examples of the usable amphoteric surfactants include carbobetaines, phosphobetaines, sulfobetaines, and imidazoliniumbetaines. Examples of the usable nonionic surfactants include polyoxyalkylene adducts; polyoxypropylene-polyoxyethylene adducts; amine oxides; mono- or di-ethanol amides; polyhydric alcohol siries such as sorbitan fatty acid esters, polyoxyethylene hardened castor oil and its fatty acid esters, polyethylene glycol fatty acid esters, glycerol fatty acid esters, sucrose fatty acid esters, alkyl saccharides, and N-polyhydroxyalkyl fatty acid amides.

Among the surfactants mentioned above, nonionic surfactants are preferable because of their excellent emulsifying ability. Among them, nonionic surfactans are preferably used in view of emulsifier dispersiblity, in particular, a polyoxyethylene glycerol tri-fatty acid ester represented by the following general formula (XII) is most preferable since which improves compatibility with the ether compound mentioned the above and facility of the formulfation to be easy.

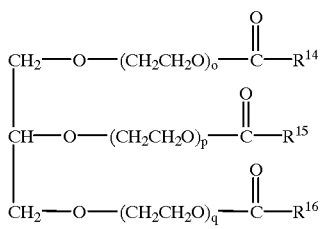

[wherein $R^{14}$, $R^{15}$, and $R^{16}$ are straight or branched alkyl group having 8 to 20 carbon atoms, being same or different from each other; and o+p+q represents average number of 5 to 50.]

Among these polyoxyethylene glycerol tri-fatty acid esters represented by the formula (XII), those, in which all of the fatty acid residues are 2-hexyldecanoic acid residue, 2-heptylundecanoic acid residue, Emery-type isostearic acid residue, or Nissan-type isostearic acid residue, are preferable since they have less oily touch and give better feeling to the skin.

The blending amount of the polyoxyethylene glycerol tri-fatty acid ester (XII) has no particular limitation, while the weight ratio of the ether compound (I), (I)/(XII), is preferably 0.2 to 20, more preferably 0.5 to 20; giving better detergency and emulsifiability in water, which are favorable for easy formulation.

In the present invention, the mixture of the ether compound and the polyoxyethylene glycerol tri-fatty acid ester (XII) can be in any forms of a uniform solution, an emulsion, or an separated two-phase composition.

Examples of the liquid state oil, an optional component used in the present invention, include: hydrocarbons such as fluid paraffin and polyisobutene; higher alcohols such as octadodecanol; synthetic ester oils such as isopropyl palmitate and tri(2-ethylhexylic acid) triglyceride; animal and vegetable oils and fats such as olive oil, jojoba oil, and squarane; and silicone oils such as cyclopentadimethyl polysiloxane and dimethyl polysiloxane. Examples of the solid state oil include: waxes such as bees wax and candelilla wax; waxes originated from petroleum such as paraffin wax and microcrystalline wax; and higher alcohols such as cetanol.

Examples of the solvent include: alcohols such as ethanol and isopropyl alcohol; polyols such as propylene glycol, glycerol, and sorbitol; and ethers of diethyleneglycol such as diethylene glycol monoethyl ether and cellosolve.

Examples of the gelling agent include dextrin fatty acid ester, organic bentonite, and polyvalent metal salts of dialkylphosphate ester.

Examples of the drug efficacy ingredient include germicides such as vitamins, triclosan, and trichlorocarbane; anti-inflammatory agents such as dipottacium glycyrrhizinate and tocopherol acetate; dandruff prevention agents such as zinc pyrithione and octopyrox; activating agents; refrigerants such as menthol; and UV-absorbents.

Examples of the water-swelling clay includes montmorillonite, saponite, hectorite, bee gum, knipia, and smectite.

Examples of the polymer include polysaccharides such as carageenan, Xanthomonas campestris, sodium alginate, pullulan, methyl cellulose, carboxymethyl cellulose, hydroxyethyl cellulose, and hydroxypropyl cellulose; and synthetic polymers such as carboxyvinyl polymer and polyvinylpyrrolidone.

Examples of the pigment include inorganic pigments such as titanium oxide, kaolin, mica, sericite, zinc white, and talc; and powdery polymers such as polymethylmethacrylate and nylon powder.

Examples of the antiseptic agents include methylparaben and butylparaben.

Examples of the viscosity regulators include inorganic salts, polyethyleneglycol stearate, and ethanol.

The make-up cosmetics removing agent of the present invention can be produced according to normal processes, and made into any forms such as oil, cream, gel, emulsion, lotion, spray, paste, solid, and semi-solid, which may be marketed as a cleansing oil, cleansing cream, cleansing lotion, and cleansing gel according to their forms.

Effects of the Invention

The ether compound represented by formula (I) of the present invention can be advantageously used as an oil for cosmetics, detergents, and lubricants, being colorless, odorless, free from change or development of color and odor with the elapse of time, having excellent touch and being pertinently low viscosity. Further, which can be used as a surfactant of such as penetrating agents, emulsifiers, solubilizing agents, dispersing agents and detergents since exhibiting pertinently low viscosity and little sticky feeling. Among them, the ether compound represented by the general formula (II) is particularly useful as an oil solution when used in make-up cosmetics removing agent, having less oily feeling and being less irritant to eyes. In addition, the ether compound represented by the general formula (VI) is particularly useful as a surfactant of penetrating agents, emulsifiers, solubilizing agents, dispersing agents, and detergents.

The make-up cosmetics removing agent composition of the present invention exhibits high detergency to solid soil such as solid fats and polymers, good touch with comfortable feeling when applied to skin, little irritation to eyes, and easiness in formulation to emulsify or gelate.

EXAMPLES

The present invention will now be explained in more details with referring to examples. However, the present invention is not limited by these examples.

Example 1

Synthesis of 1,3-dimethyl butyl dodecyl ether $CH_3$—$CH(CH_3)$—$CH_2$—$CH(CH_3)$—$O$—$(CH_2)_{11}$—$CH_3$ 93 g (0.5 mol) of dodecyl alcohol, 100 g (1.0 mol) of 4-methyl-2-pentanone and 1.9 g of 5% Pd-C (pH 6.6) as a catalyst were charged into a 500 ml autoclave equipped with an inlet pipe for hydrogen gas and a stirrer, and were stirred for 8 hours at 150° C. under a hydrogen pressure of 100 kg/cm$^2$.

The catalyst was removed by filtration after the completion of the reaction. Excessive amount of 4-methyl-2-pentanone was removed under vacuum. A transparent colorless liquid of 1,3-dimethyl butyl dodecyl ether, the target product, in an amount of 108 g (0.40 mol) was obtained by vacuum distillation under 120 to 122° C./1 torr.

The isolation yield was 80%.

The $^1$H-NMR data of produced 1,3-dimethyl butyl dodecyl ether is shown in below.

$^1$H-NMR (δ; ppm, CDCl$_3$); 0.82–0.98 (overlapped doublet and triplet, 9H; a); 1.12 (doublet, 3H; b); 1.20–1.40 (broad singlet, 18H; c); 1.40–1.65 (complicated multiplet, 4H; d); 1.65–1.87 (complicated multiplet, 1H; e); 3.24–3.40 (complicated multiplet, 1H; f); 3.38–3.60 (complicated multiplet, 2H; g);

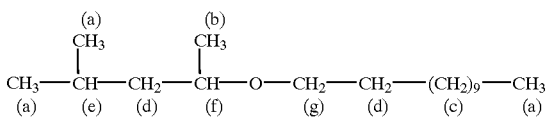

Example 2
Synthesis of 1,3-dimethyl butyl dodecyl ether 74.1 g (0.7 mol) of 4-Methyl-2-pentanol and 36 g (0.9 mol) of sodium hydroxide pellet were charged into a 500 ml flask with a tap funnel equipped with a cooling tube and an inlet pipe for nitrogen gas and an stirrer, and were stirred for 1 hours at 80° C. with introduction of nitrogen. Thereafter, 224 g (0.9 mol) of dodecyl bromide was added dropwise to the mixture in 1 hour, and the mixture was heated up to 100° C. and stirred for 16 hours.

After completion of the reaction, the excess sodium hydroxide and resulting salt was removed from the reaction mixture by water washing, then the excess 4-methyl-2-pentanol and dodecyl bromide were removed under vacuum, and further vacuum distillation (102° C./0.25 torr) was applied; thereby, the target product, 1,3-dimethyl butyl dodecyl ether in an amount of 40 g (0.15 mol) was obtained as a transparent colorless liquid.

The isolation yield was 21%.

The $^1$H-NMR data of the product 1,3-dimethyl butyl dodecyl ether was the same as of those of the example 1.

Example 3
Synthesis of 1,3-dimethyl butyl tetradecyl ether $CH_3—CH(CH_3)—CH_2—CH(CH_3)—O—(CH_2)_{13}—CH_3$ 107 g (0.5 mol) of tetradecyl alcohol, 100 g (1.0 mol) of 4-methyl-2-pentanone and 2.1 g of 5% Pd-C (pH 6.6) as a catalyst were charged into a 500 ml autoclave equipped with an inlet pipe for hydrogen gas and a stirrer, and were stirred for 8 hours at 150° C. under a hydrogen pressure of 100 kg/cm².

The catalyst was removed by filtration after completion of the reaction and excessive amount of 4-methyl-2-pentanone was then removed under vacuum, and further vacuum distillation (143° C./1 torr) was applied; thereby, the target product, 1,3-dimethyl butyl tetradecyl ether, in an amount of 112 g (0.38 mol) was obtained as a transparent colorless liquid.

The isolation yield was 75%.

The $^1$H-NMR data of the product 1,3-dimethyl butyl tetradecyl ether is shown in below.

$^1$H-NMR (d; ppm, CDCl$_3$); 0.85–1.05 (overlapped doublet and triplet, 9H; a); 1.15 (doublet, 3H; b); 1.20–1.45 (broad singlet, 22H; c); 1.45–1.65 (complicated multiplet, 4H; d); 1.65–1.90 (complicated multiplet, 1H; e); 3.25–3.45 (complicated multiplet, 1H; f); 3.37–3.10 (complicated multiplet, 2H; g)

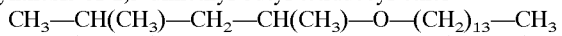

Example 4
Synthesis of 1,3-dimethyl butyl tetradecyl ether 107 g (0.5 mol) of tetradecyl alcohol, 100 g (1.0 mol) of 4-methyl-2-pentanone and 5.35 g of 2% Pd(OH)$_2$-C as a catalyst were charged into a 500 ml autoclave equipped with an inlet pipe for hydrogen gas and a stirrer, and were stirred for 8 hours at 150° C. under a hydrogen pressure of 100 kg/cm².

The catalyst was removed by filtration after the completion of the reaction. Excessive amount of 4-methyl-2-pentanone was removed under vacuum. Further vacuum distillation was applied in the same way as Example 3; thereby, the target product, 1,3-dimethyl butyl tetradecyl ether in an amount of 39 g (0.13 mol) was obtained as a transparent colorless liquid. The isolation yield was 26%.

In this example, the catalyst used was previously washed thoroughly with water, and washed with ethanol then completely dried.

Example 5
Synthesis of 1,3-dimethyl butyl tetradecyl ether 107 g (0.5 mol) of tetradecyl alcohol, 100 g (1.0 mol) of 4-methyl-2-pentanone and 2.1 g of 5% Pd-zeolite (pH 6.47) as a catalyst were charged into a 500 ml autoclave equipped with an inlet pipe for hydrogen gas and a stirrer, and were stirred for 8 hours at 150° C. under a hydrogen pressure of 100 kg/cm².

The catalyst was removed by filtration after the completion of the reaction. Excessive amount of 4-methyl-2-pentanone was removed under vacuum. Further vacuum distillation was applied in the same way as Example 3; thereby, the target product, 1,3-dimethyl butyl tetradecyl ether in an amount of 28 g (0.095 mol) was obtained as a transparent colorless liquid. The isolation yield was 19%.

Example 6
Synthesis of 1,3-dimethyl butyl tetradecyl ether 107 g (0.5 mol) of tetradecyl alcohol, 100 g (1.0 mol) of 4-methyl-2-pentanone and 2.1 g of 5% Pd-alumina silicate (pH 7.97) as a catalyst were charged into a 500 ml autoclave equipped with an inlet pipe for hydrogen gas and an stirrer, and were stirred for 8 hours at 150° C. under a hydrogen pressure of 100 kg/cm².

The catalyst was removed by filtration after the completion of the reaction. Excessive amount of 4-methyl-2-pentanone was removed under vacuum. Then, by silica gel column chromatography, the target product, 1,3-dimethyl butyl tetradecyl ether in an amount of 3.0 g (0.01 mol) was obtained as a transparent colorless liquid. The isolation yield was 2%.

Example 7
Synthesis of 1,3-dimethyl butyl tetradecyl ether 107 g (0.5 mol) of tetradecyl alcohol, 100 g (1.0 mol) of 4-methyl-2-pentanone and 2.1 g of 5% Pd-alumina (pH 5.00) as a catalyst were charged into a 500 ml autoclave equipped with an inlet pipe for hydrogen gas and a stirrer, and were stirred for 8 hours at 150° C. under a hydrogen pressure of 100 kg/cm².

The catalyst was removed by filtration after the completion of the reaction. Excessive amount of 4-methyl-2-pentanone was removed under vacuum. Further vacuum distillation was applied in the same way as Example 3; thereby, the target product, 1,3-dimethyl butyl tetradecyl ether in an amount of 33 g (0.11 mol) was obtained as a transparent colorless liquid. The isolation yield was 22%.

Example 8
Synthesis of 1,3-dimethyl butyl tetradecyl ether 107 g (0.5 mol) of tetradecyl alcohol, 100 g (1.0 mol) of 4-methyl-2-pentanone and 2.1 g of 5% Pd-C (pH 10.26) as a catalyst were charged into a 500 ml autoclave equipped with an inlet pipe for hydrogen gas and a stirrer, and were stirred for 8 hours at 150° C. under a hydrogen pressure of 100 kg/cm².

The catalyst was removed by filtration after the completion of the reaction. Excessive amount of 4-methyl-2-pentanone was removed under vacuum. Further vacuum distillation was applied in the same way as Example 3; thereby, the target product, 1,3-dimethyl butyl tetradecyl ether in an amount of 28 g (0.094 mol) was obtained as a transparent colorless liquid. The isolation yield was 19%.

Example 9

Synthesis of 1,3-dimethyl butyl hexadecyl ether

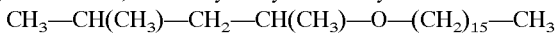

121 g (0.5 mol) of hexadecyl alcohol, 100 g (0.5 mol) of 4-methyl-2-pentanone and 2.4 g of 5% Pd-C (pH 6.6) as a catalyst were charged into a 500 ml autoclave equipped with an inlet pipe for hydrogen gas and a stirrer, and were stirred for 8 hours at 150° C. under a hydrogen pressure of 100 kg/cm².

The catalyst was removed by filtration after the completion of the reaction. Excessive amount of 4-methyl-2-pentanone was removed under vacuum, and further vacuum distillation (142° C./0.6 torr) was applied; thereby, the target product, 1,3-dimethyl butyl hexadecyl ether in an amount of 114 g (0.35 mol) was obtained as a transparent colorless liquid.

The isolation yield was 70%.

The $^1$H-NMR data of the product 1,3-dimethyl butyl hexadecyl ether is shown in below.

$^1$H-NMR (δ; ppm, CDCl₃); 0.80–1.05 (overlapped doublet and triplet, 9H; a); 1.11 (doublet, 3H; b); 1.17–1.40 (broad singlet, 26H; c); 1.40–1.65 (complicated multiplet, 4H; d); 1.65–1.90 (complicated multiplet, 1H; e); 3.20–3.40 (complicated multiplet, 1H; f); 3.35–3.60 (complicated multiplet, 2H; g);

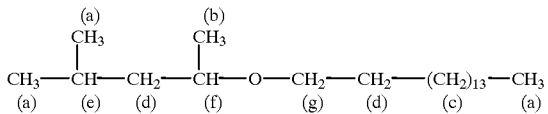

Example 10

Synthesis of 1,3-dimethyl butyl octadecyl ether

CH₃—CH(CH₃)—CH₂—CH(CH₃)—O—(CH₂)₁₇—CH₃

108 g (0.4 mol) of octadecyl alcohol, 80 g (0.8 mol) of 4-methyl-2-pentanone and 2.2 g of 5% Pd-C (pH 4.0) as a catalyst were charged into a 500 ml autoclave equipped with an inlet pipe for hydrogen gas and a stirrer, and were stirred for 8 hours at 150° C. under a hydrogen pressure of 100 kg/cm².

The catalyst was removed by filtration after the completion of the reaction. Excessive amount of 4-methyl-2-pentanone was removed under vacuum. By silica gel column chromatography refining, the target product, 1,3-dimethyl butyl octadecyl ether in an amount of 106 g (0.30 mol) was obtained as a transparent colorless liquid.

The isolation yield was 75%.

The $^1$H-NMR data of the product 1,3-dimethyl butyl octadecyl ether is shown in below.

$^1$H-NMR (δ; ppm, CDCl₃); 0.85–0.95 (overlapped doublet and triplet, 9H; a); 1.12 (doublet, 3H; b); 1.20–1.40 (broad singlet, 30H; c); 1.40–1.65 (complicated multiplet, 4H; d); 1.65–1.87 (complicated multiplet, 1H; e); 3.28–3.40 (complicated multiplet, 1H; f); 3.37–3.60 (complicated multiplet, 2H; g);

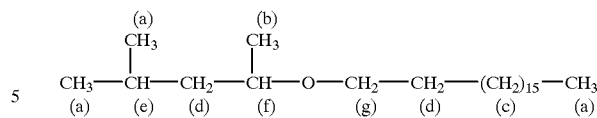

Example 11

Synthesis of 1,3-dimethyl butyl octadecyl ether 51 g (0.5 mol) of 4-metyl-2-pentanol and 26 g (0.65 mol) of sodium hydroxide pellet were charged into a 500 ml flask with a tap funnel equipped with a cooling tube and an inlet pipe for nitrogen gas and a stirrer, and were stirred for 1 hours at 80° C. with introduction of nitrogen. Thereafter, octadecyl bromide in an amount of 216 g (0.65 mol) was added dropwise to the mixture in 1 hour, and the mixture was heated up to 100° C. and stirred for 20 hours.

After the completion of the reaction, the excess sodium hydroxide and resulting salt was removed from the reaction mixture by water washing, then the excess 4-methyl-2-pentanol, and octadecyl bromide were removed under vacuum. By silica gel column chromatography refining, the target product, 1,3-dimethyl butyl octadecyl ether, in an amount of 27 g (0.075 mol) was obtained as a transparent colorless liquid.

The isolation yield was 15%.

The $^1$H-NMR data of the resulting 1,3-dimethyl butyl octadecyl ether was the same as those of the example 10.

Example 12

Synthesis of isopropyl hexadecyl ether

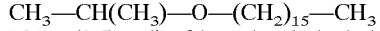

121 g (0.5 mol) of hexadecyl alcohol, 87 g (1.5 mol) of acetone and 2.1 g of 5% Pd-C (pH 4.0) as a catalyst were charged into a 500 ml autoclave equipped with an inlet pipe for hydrogen gas and a stirred, and were stirred for 8 hours at 150° C. under a hydrogen pressure of 100 kg/cm².

The catalyst was removed by filtration after the completion of the reaction. Excessive amount of acetone was removed under vacuum. By silica gel column chromatography refining, the target product, isopropyl hexadecyl ether in an amount of 92 g (0.36 mol) was obtained as a transparent colorless liquid.

The isolation yield was 72%.

The $^1$H-NMR data of the product isopropyl hexadecyl ether is shown in below.

$^1$H-NMR (δ; ppm, CDCl₃); 0.90 (triplet, 3H; a); 1.17 (doublet, 6H; b); 1.20–1.40 (broad singlet, 26H; c); 1.45–1.68 (complicated multiplet, 2H; d); 3.40 (triple line, 2H; e); 3.45–3.64 (complicated multiplet, 1H; f);

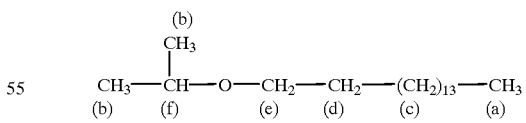

Example 13

Synthesis of 1-methyl propyl tetradecyl ether

CH₃—CH₂—CH(CH₃)—O—(CH₂)₁₃—CH₃

127 g (0.4 mol) of tetradecyl alcohol, 107 g (0.5 mol) of methyl ethyl ketone and 2.1 g of 5% Pd-C (pH 4.0) as a catalyst were charged into a 500 ml autoclave equipped with an inlet pipe for hydrogen gas and a stirrer, and were stirred for 8 hours at 150° C. under a hydrogen pressure of 100 kg/cm².

The catalyst was removed by filtration after the completion of the reaction. Excessive amount of methyl ethyl ketone was removed under vacuum. Further, by silica gel column chromatography refining, the target product, 1-methyl propyl tetradecyl ether in an amount of 103 g (0.38 mol) was obtained as a transparent colorless liquid.

The isolation yield was 76%.

The $^1$H-NMR data of the product 1-methyl propyl tetradecyl ether is shown in below.

$^1$H-NMR (δ; ppm, CDCl$_3$); 0.72–0.98 (two triplets, 6H; a); 1.13 (doublet, 3H; b); 1.20–1.40 (broad singlet, 22H; c); 1.40–1.70 (complicated multiplet, 4H; d); 3.20–3.40 (complicated multiplet, 2H; e); 3.35–3.55 (complicated multiplet, 1H; f);

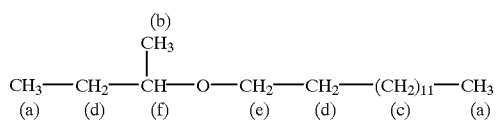

Example 14
Synthesis of 1-methyl propyl tetradecyl ether 37 g (0.5 mol) of 2-butanol and 32 g (0.8 mol) of sodium hydroxide pellet were charged into a 500 ml flask with a tap funnel equipped with a cooling tube and an inlet pipe for nitrogen gas and a stirrer, and were stirred for 1 hours at 80° C. with introduction of nitrogen. Thereafter, tetradecyl bromide in an amount of 222 g (0.8 mol) was added dropwise to the mixture in 1 hour, and the mixture was heated up to 100° C. and stirred for 20 hours.

After the completion of the reaction, the excess sodium hydroxide and resulting salt was removed from the reaction mixture by water washing, then the excess 2-butanol, and tetradecyl bromide were removed under vacuum. Further, by silica gel column chromatography refining, the target product, 1-methyl propyl tetradecyl ether in an amount of 35 g (0.13 mol) was obtained as a transparent colorless liquid. The isolation yield was 25%.

The $^1$H-NMR data of the product 1-methyl propyl tetradecyl ether was the same as those of the example 13.

Example 15
Synthesis of 1-methyl propyl octadecyl ether

CH$_3$—CH$_2$—CH(CH$_3$)—O—(CH$_2$)$_{17}$—CH$_3$ 135 g (0.5 mol) of octadecyl alcohol, 100 g (1.0 mol) of methyl ethyl ketone and 2.7 g of 5% Pd-C (pH 4.0) as a catalyst were charged into a 500 ml autoclave equipped with an inlet pipe for hydrogen gas and a stirrer, and were stirred for 8 hours at 150° C. under a hydrogen pressure of 100 kg/cm$^2$.

The catalyst was removed by the filtration after the completion of the reaction. Excessive amount of methyl ethyl ketone was removed under vacuum, and further vacuum distillation (160° C./0.35 torr) was applied; thereby, the target product, 1-methyl propyl octadecyl ether in an amount of 109 g (0.33 mol) was obtained as a transparent colorless liquid.

The isolation yield was 66%.

The $^1$H-NMR data of the product 1-methyl propyl octadecyl ether is shown in below.

$^1$H-NMR (δ; ppm, CDCl$_3$); 0.84–1.00 (two triple lines, 6H; a); 1.13 (doublet, 3H; b); 1.20–1.43 (broad singlet, 30H; c); 1.43–1.70 (complicated multiplet, 4H; d); 3.20–3.43 (complicated multiplet, 2H; e); 3.36–3.57 (complicated multiplet, 1H; f);

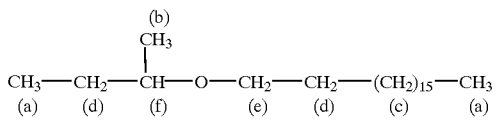

Example 16
Synthesis of cyclohexyl tetradecyl ether

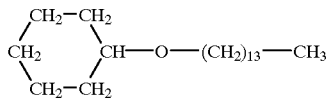

107 g (0.5 mol) of tetradecyl alcohol, 98 g (1.0 mol) of cyclohexanone and 2.1 g of 5% Pd-C (pH 4.0) as a catalyst were charged into a 500 ml autoclave equipped with an inlet pipe for hydrogen gas and a stirrer, and were stirred for 8 hours at 150° C. under a hydrogen pressure of 100 kg/cm$^2$.

The catalyst was removed by filtration after the completion of the reaction. Excessive amount of cyclohexanone was then removed under vacuum., and further vacuum distillation (148° C./0.6 torr) was applied; thereby, the target product, cyclohexyl tetradecyl ether in an amount of 110 g (0.37 mol) was obtained as a transparent colorless liquid.

The isolation yield was 74%.

The $^1$H-NMR data of the product cyclohexyl tetradecyl ether is shown in below.

$^1$H-NMR (δ; ppm, CDCl$_3$); 0.87 (triplet, 3H; a); 1.15–2.00 (one broad singlet and three complex multiplets 34H; b); 3.10–3.40 (complicated multiplet, 1H; c); 3.51 (triple line, 2H; d);

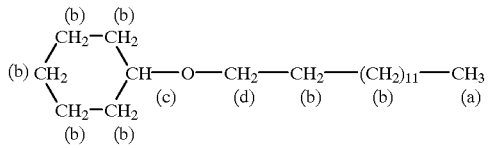

Example 17
Synthesis of ethylene glycol-1-methyl propyl butyl ether

CH$_3$—CH$_2$—CH(CH$_3$)—O—CH$_2$—CH$_2$—O—CH$_2$—CH$_2$—CH$_3$ 81 g (0.7 mol) of ethylene glycol monobutyl ether, 101 g (1.4 mol) of methyl ethyl ketone and 1.16 g of 5% Pd-C (pH 4.0) as a catalyst were charged into a 500 ml autoclave equipped with an inlet pipe for hydrogen gas and a stirrer, and were stirred for 8 hours at 150° C. under a hydrogen pressure of 100 kg/cm$^2$.

The catalyst was removed by filtration after the completion of the reaction. Excessive amount of methylethyl ketone was removed under vacuum. By water washing of unreacted ethylene glycol monobutyl ether, the target product, ethylene glycol-1-methyl propyl butyl ether in an amount of 100 g (0.58 mol) was obtained as a transparent colorless liquid.

The isolation yield was 83%.

The $^1$H-NMR data of the product ethylene glycol-1-methyl propyl butyl ether is shown in below.

$^1$H-NMR (δ; ppm, CDCl$_3$); 0.85–1.12 (complicated multiplet, 6H; a); 1.12–1.28 (doublet, 3H; b); 1.28–1.85 (complicated multiplet, 6H; c); 3.25–3.90 (complicated multiplet, 7H; d);

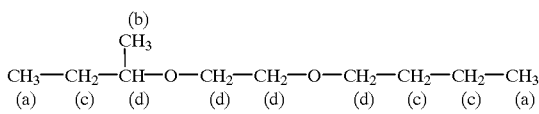

Example 18

Synthesis of triethylene glycol isopropyl dodecyl ether

CH$_3$—CH(CH$_3$)—O—CH$_2$—CH$_2$—O—CH$_2$—CH$_2$—O—CH$_2$—CH$_2$—O—CH$_2$—(CH$_2$)$_{10}$—CH$_3$ 127 g (0.4 mol) of triethylene glycol monododecyl ether, 93 g (1.6 mol) of acetone and 2.5 g of 5% Pd-C (pH 4.0) as a catalyst were charged into a 500 ml autoclave equipped with an inlet pipe for hydrogen gas and a stirrer, and were stirred for 8 hours at 150° C. under a hydrogen pressure of 100 kg/cm$^2$.

The catalyst was removed by filtration after the completion of the reaction. Excessive amount of acetone was then removed under vacuum. By silica gel column chromatography, the target product, triethylene glycol isopropyl dodecyl ether in an amount of 112 g (0.31 mol) was obtained as a transparent colorless liquid.

The isolation yield was 78%.

The $^1$H-NMR data of the product triethylene glycol isopropyl dodecyl ether is shown in below.

$^1$H-NMR (δ; ppm, CDCl$_3$); 0.82–0.95 (triplet; 3H, a); 1.10–1.20 (doublet; 6H, b); 1.20–1.40 (broad singlet; 18H, c); 1.40–1.60 (complicated multiplet; 2H, d); 3.25–3.90 (complicated multiplet; 15H, e);

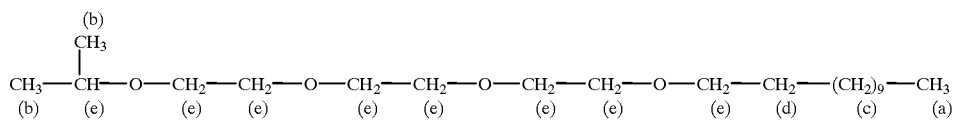

Example 19

Synthesis of polyoxyethylene (average ethylene oxides added: 6 mol) isopropyl dodecyl ether CH$_3$—CH(CH$_3$)—O—CH$_2$—CH$_2$—(O—CH$_2$—CH$_2$)$_n$—O—CH$_2$—(CH$_2$)$_{10}$—CH$_3$ n=5 (average)

polyoxyethylene (average ethylene oxides added: 6 mol) monododecyl ether in an amount of 135 g (0.3 mol), acetone in an amount of 104 g (1.8 mol) and 5% Pd-C (pH 4.0) in an amount of 2.5 g as a catalyst were charged into a 500 ml autoclave equipped with an inlet pipe for hydrogen gas and a stirrer, and were stirred for 8 hours at 150° C. under a hydrogen pressure of 100 kg/cm$^2$.

The catalyst was removed by filtration after the completion of the reaction. Excessive amount of the acetone was then removed under vacuum. By silica gel column chromatography, the target product, polyoxyethylene (average ethylene oxides added: 6 mol) isopropyl dodecyl ether, in an amount of 108 g (0.22 mol) was obtained as a transparent colorless liquid.

The isolation yield was 73%.

The $^1$H-NMR data of the product polyoxyethylene (average ethylene oxides added: 6 mol) isopropyl dodecyl ether is shown in below.

$^1$H-NMR (δ; ppm, CDCl$_3$); 0.82–0.95 (triplet; 3H, a); 1.10–1.20 (doublet; 6H, b); 1.20–1.40 (broad singlet; 18H, c); 1.40–1.60 (complicated multiplet; 2H, d); 3.25–3.90 (complicated multiplet; 27H, e);

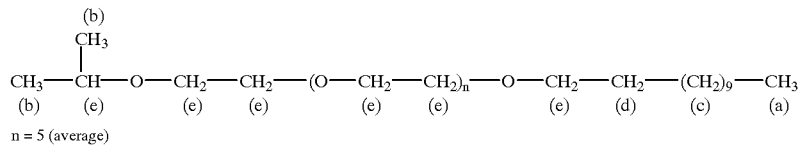

n = 5 (average)

Example 20

Synthesis of triethylene glycol-1-methyl propyl dodecyl ether

CH$_3$—CH$_2$—CH(CH$_3$)—O—CH$_2$—CH$_2$—O—CH$_2$—CH$_2$—O—CH$_2$—CH$_2$—O—CH$_2$—(CH$_2$)$_{10}$—CH$_3$ 127 g (0.4 mol) of triethylene glycol monododecyl ether, 58 g (0.8 mol) of methyl ethyl ketone and 2.5 g of 5% Pd-C (pH 4.0) as a catalyst were charged into a 500 ml autoclave equipped with an inlet pipe for hydrogen gas and a stirrer, and were stirred for 8 hours at 150° C. under a hydrogen pressure of 100 kg/cm$^2$.

The catalyst was removed by filtration after the completion of the reaction. Excessive amount of methyl ethyl ketone was then removed under vacuum. By silica gel column chromatography, the target product, triethylene glycol-1-methyl propyl dodecyl ether in an amount of 112 g (0.3 mol) was obtained as a transparent colorless liquid.

The isolation yield was 75%.

The $^1$H-NMR data of the product triethylene glycol-1-methyl propyl dodecyl ether is shown in below.

$^1$H-NMR (δ; ppm, CDCl$_3$); 0.85–1.10 (two triplets; 6H, a); 1.10–1.20 (doublet; 3H, b); 1.20–1.85 (broad singlet and complicated multiplet; 22H, c); 3.25–3.90 (complicated multiplet; 15H, d);

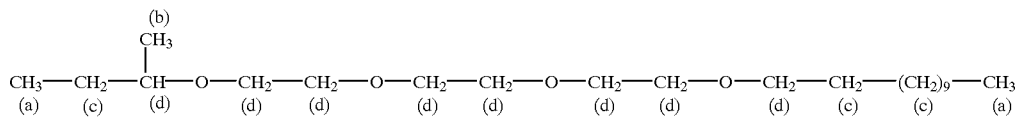

Example 21

Synthesis of triethylene glycol-1,3-dimethyl butyl dodecyl ether $CH_3—CH(CH_3)—CH_2—CH(CH_3)—O—CH_2—CH_2—O—CH_2—CH_2—O—CH_2—CH_2—O—CH_2—(CH_2)_{10}—CH_3$ 127 g (0.4 mol) of triethylene glycol monododecyl ether, 80 g (0.8 mol) of methyl isobutyl ketone and 2.5 g of 5% Pd-C (pH 4.0) as a catalyst were charged into a 500 ml autoclave equipped with an inlet pipe for hydrogen gas and a stirrer, and were stirred for 8 hours at 150° C. under 100 kg/cm² hydrogen pressure.

The catalyst was removed by filtration after the completion of the reaction. Excessive amount of methyl isobutyl ketone was then removed under vacuum. By silica gel column chromatography, the target product, triethylene glycol-1,3-dimethyl butyl dodecyl ether in an amount of 112 g (0.28 mol) was obtained as a transparent colorless liquid.

The isolation was made with a yield of 70%.

The $^1$H-NMR data of the product triethylene glycol-1,3-dimethyl butyl dodecyl ether is shown in below.

$^1$H-NMR (δ; ppm, CDCl$_3$); 0.80–1.05 (overlapped doublet and triplet; 9H, a); 1.10 (doublet; 3H, b); 1.17–1.40 (broad singlet; 18H, c); 1.40–1.90 (complicated multiplet; 5H, d); 3.25–3.90 (complicated multiplet; 15H, e);

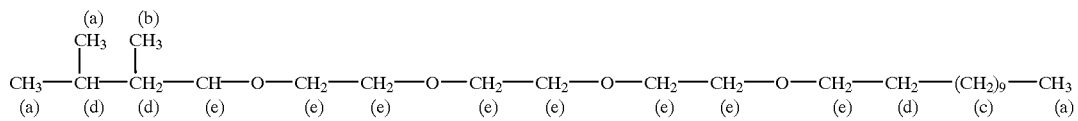

Example 22

Synthesis of polyoxyethylene (average ethylene oxides added: 9 mol)-1-methyl propyl dodecyl ether $CH_3—CH_2—CH(CH_3)—O—(CH_2—CH_2—O)_n—CH_2—CH_2—(CH_2)_9—CH_3$ $_{CH3}$ $—CH_2—CH(CH_3)—O—(CH_2—CH_2—O)_n—CH_2—CH_2—(CH_2)_9—CH_3$ n=9 (average)

An adduct of dodecyl alcohol with ethylene oxide (average ethylene oxides added: 9 mol) in an amount of 200 g (0.34 mol), methyl ethyl ketone in an amount of 97 g (1.34 mol) and 5% Pd-C (pH 4.0) in an amount of 4 g as a catalyst were charged into a 1 liter autoclave equipped with an inlet pipe for hydrogen gas and a stirrer, and were reacted for 7 hours at 150° C. under a hydrogen pressure of 100 kg/cm².

The catalyst was removed by filtration after the completion of the reaction. Excessive amount of methyl ethyl ketone was then removed under vacuum. By silica gel column chromatography, the target product, polyoxyethylene (average ethylene oxides added: 9 mol)-1-methyl propyl dodecyl ether, in an amount of 202 g was obtained.

The etherification percentage was found to be 73% by measuring the hydroxyl value.

$^1$H-NMR (δ; ppm, CDCl$_3$); 0.83(m, 6H, a), 1.15 (d, 3H, b), 1.27 (broad, 18H, c), 1.58 (broad, 4H, d), 3.51 (broad, 3H, e), 3.65 (m, 36H, f);

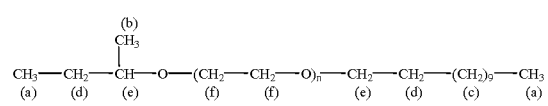

Example 23

Synthesis of polyoxyethylene (average ethylene oxides added: 9 mol)-1,3-dimethyl butyl dodecyl ether $CH_3—CH(CH_3)—CH_2—CH(CH_3)—O—(CH_2—CH_2—O)_n—CH_2—CH_2—(CH_2)_9—CH_3$ n=9 (average)

An ethylene oxide adduct (average ethylene oxides added: 9 mol) with dodecyl alcohol in an amount of 150 g (0.26 mol), methyl isobutyl ketone in an amount of 350 g (3.5 mol) and 5% Pd-C (pH 4.0) in an amount of 6 g as a catalyst were charged into a 1 liter autoclave equipped with an inlet pipe for hydrogen gas and a stirrer, and were reacted for 7 hours at 150° C. under a hydrogen pressure of 100 kg/cm². The catalyst was removed by filtration after the completion of the reaction. Excessive amount of the methyl isobutyl ketone was then removed under vacuum. The target product, polyoxyethylene (average ethylene oxides added: 9 mol)-1,3-dimethyl butyl dodecyl ether, in an amount of 167 g was thus obtained. The etherification percentage was found to be 71% by measuring the hydroxyl value.

$^1$H-NMR (δ; ppm, CDCl$_3$); 0.81 (m, 9H, a), 1.12 (d, 3H, b), 1.25 (broad, 18H, c), 1.55 (broad, 4H, d), 1.70 (m, 1H, e), 3.50 (broad, 3H, f), 3.61 (m, 36H, g)

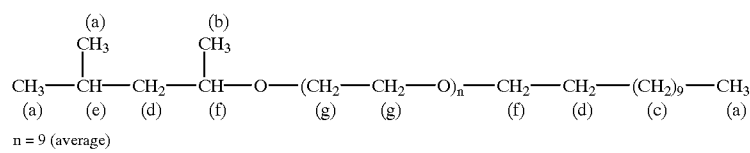

n = 9 (average)

Example 24
Synthesis of polyoxyethylene (average ethylene oxides added: 20 mol)-isopropyl dodecyl ether $CH_3—CH(CH_3)—O—(CH_2—CH_2O)_n—CH_2—CH_2—(CH_2)_9—CH_3$ n=20 (average)

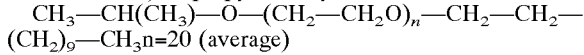

An adduct of dodecyl alcohol with ethylene oxide (average 20 mol ethylene oxides added) in an amount of 200 g (0.19 mol), acetone in an amount of 165 g (2.84 mol) and 5% Pd-C (pH 4.0) in an amount of 4 g as a catalyst were charged into a 1 liter autoclave equipped with an inlet pipe for hydrogen gas and a stirrer, and were reacted for 6 hours at 150° C. under a hydrogen pressure of 100 kg/cm². The catalyst was removed by filtration after the completion of the reaction. Excessive amount of the acetone was then removed under vacuum. The target product, polyoxyethylene (average ethylene oxides added: 20 mol)-isopropyl dodecyl ether in an amount of 200 g was thus obtained. The etherification percentage was found to be 76% by measuring the hydroxyl value.

$^1$H-NMR (δ; ppm, CDCl$_3$); 0.84 (t, 3H, a), 1.17 (d, 6H, b), 1.29 (broad, 18H, c), 1.59 (m, 2H, d), 3.52 (broad, 3H, e), 3.66 (m, 80H, f)

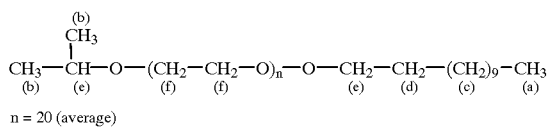

n = 20 (average)

Example 25
Synthesis of polyoxyethylene (average ethylene oxides added: 12 mol)-3,7-dimethyl octyl dodecyl ether $CH_3—CH(CH_3)CH_2CH_2CH_2—CH(CH_3)CH_2CH_2—O—(CH_2—CH_2—O)_n—CH_2—CH_2—(CH_2)_9—CH_3$ n=12 (average)

An adduct of dodecyl alcohol with ethylene oxide (average ethylene oxides added: 12 mol) in an amount of 200 g (0.28 mol), citronellal in an amount of 345 g (2.24 mol) and 5% Pd-C (pH 4.0) in an amount of 6 g as a catalyst were charged into a 1 liter autoclave equipped with an inlet pipe for hydrogen gas and a stirrer, and were reacted for 6 hours at 150° C. a hydrogen pressure of 100 kg/cm². The catalyst was removed by filtration after the completion of the reaction. Excessive amount of the citronella oil was then removed under vacuum. The target product, polyoxyethylene (average ethylene oxides added: 12 mol)-3,7-dimethyl octyl dodecyl ether in an amount of 218 g was thus obtained. The etherification percentage was found to be 72.1% by measuring the hydroxyl value.

$^1$H-NMR (δ; ppm, CDCl$_3$); 0.81 (m, 12H, a), 1.27 (broad, 24H, b), 1.55 (broad, 4H, c), 1.72 (m, 2H, d), 3.51 (m, 4H, e), 3.65 (m, 48H, f)

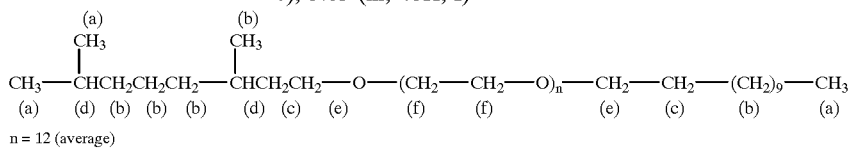

Example 26

Synthesis of polyoxyethylene (average ethylene oxides added: 9 mol)-1-isobutyl-3-methyl butyl dodecyl ether

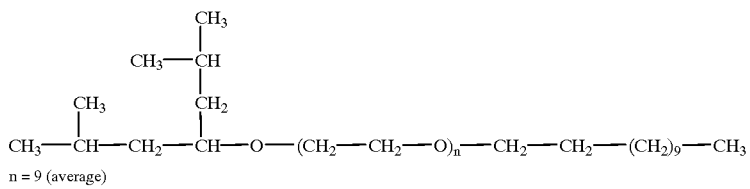

n = 9 (average)

An adduct of dodecyl alcohol with ethylene oxide (average ethylene oxides added: 9 mol) with dodecyl alcohol in an amount of 150 g (0.26 mol), diisobutyl ketone in an amount of 293 g (2.1 mol) and 5% Pd-C (pH 4.0) in an amount of 6 g as a catalyst were charged into a 1 liter autoclave equipped with an inlet pipe for hydrogen gas and a stirrer, and were reacted for 8 hours at 150° C. under a hydrogen pressure of 100 kg/cm². The catalyst was removed by filtration after the completion of the reaction. Excessive amount of the diisobutyl ketone was then removed under vacuum. The target product, polyoxyethylene (average ethylene oxides added: 9 mol)-1-isobutyl-3-methyl butyl dodecyl ether in an amount of 159 g was thus obtained. The etherification percentage was found to be 75% by measuring the hydroxyl value.

$^1$H-NMR (δ; ppm, CDCl$_3$); 0.87 (m, 15H, a), 1.29 (broad, 18H, b), 1.57 (broad, 6H, c), 1.69 (m, 2H, d), 3.50 (m, 3H, e), 3.63 (m, 36H, f)

$$CH_3\underset{(a)}{-}\underset{|}{CH}\underset{(d)}{-}CH_2\underset{(c)}{-}\underset{|}{CH}\underset{(e)}{-}O-(CH_2-CH_2-O)_n-CH_2-CH_2-(CH_2)_9-CH_3$$
with branches: $CH_3$ (a), $CH_3$ (a) on $CH$ (a)$-CH(d)-CH_2(c)$ arrangement n = 9 (average)

Example 27
Synthesis of polyoxyethylene (average ethylene oxides added: 9 mol)-1-methyl heptyl dodecyl ether $$CH_3CH_2CH_2CH_2CH_2CH_2-\underset{|}{CH}-O-(CH_2-CH_2-O)_n-CH_2-CH_2-(CH_2)_9-CH_3$$
with $CH_3$ branch on the CH n = 9 (average)

An adduct of dodecyl alcohol with ethylene oxide (average ethylene oxides added: 9 mol) in an amount of 150 g (0.26 mol), methyl n-hexyl ketone in an amount of 262 g (2.1 mol) and 5% Pd-C (pH 4.0) 6 g as a catalyst were charged into a 1 liter autoclave equipped with an inlet pipe for hydrogen gas and a stirrer, and were reacted for 7 hours at 150° C. under a hydrogen pressure of 100 kg/cm$^2$. The catalyst was removed by filtration after the completion of reaction. Excessive amount of the methyl heptenone was then removed under vacuum. The target product, polyoxyethylene (average ethylene oxides added: 9 mol)-1-methyl heptyl dodecyl ether in an amount of 152 g was thus obtained. The etherification percentage was found to be 76% by measuring the hydroxyl value.

$^1$H-NMR (δ; ppm, CDCl$_3$); 0.81 (m, 6H, a), 1.14 (d, 3H, b), 1.26 (broad, 26H, c), 1.55 (broad, 4H, d), 3.49 (broad, 3H, e), 3.60 (broad, 36H, f)

$$CH_3CH_2CH_2CH_2CH_2CH_2-CH-O-(CH_2-CH_2-O)_n-CH_2-CH_2-(CH_2)_9-CH_3$$
(a) (c) (c) (c) (c) (d)   (e)    (f)    (f)    (e)    (d)    (c)    (a)
with (b) $CH_3$ branch n = 9 (average)

Test Example 1

Odor, change in color and odor with the elapse of time, touch and viscosity, of ether compounds obtained in Examples 1, 3, 9, 10, 12, 13, 15 and 22 according to the present invention, were evaluated by the following method.

A general purpose oil solution shown in Table 1 as control was also evaluated in the same manner.

These results are shown in Table 1.

Evaluation Method
(1) Evaluation criterion for odor

0: No odor

Δ: Slight odor x: Odor (2) Evaluation criterion for change in color and odor standing at 50° C. for one week 0: No change Δ: Slight change x: Change observed (3) Evaluation criterion for touch 0: Not sticky Δ: Slightly sticky x: Sticky (4) Evaluation criterion for viscosity 0: Less than 10 cps (satisfactorily extendable)

Δ: 10–20 cps (fairly extendable)

x: More than 20 cps (poorly extendable)

TABLE 1

|  |  | (1) Odor | (2) Change with elaps of time | (3) Texture | (4) Viscosity |
|---|---|---|---|---|---|
| Invention product | 1,3-dimethylbutyldodecylether (Ex. 1) | ○ | ○ | ○ | ○ |
|  | 1,3-dimethylbutyltetradecylether (Ex. 3) | ○ | ○ | ○ | ○ |
|  | 1,3-dimethylbutylhexadecylether (Ex. 9) | ○ | ○ | ○ | ○ |

TABLE 1-continued

|  | | (1) Odor | (2) Change with elaps of time | (3) Texture | (4) Viscosity |
|---|---|---|---|---|---|
| | 1,3-dimethylbutyloctadecylether (Ex. 10) | ○ | ○ | ○ | ○ |
| | isopropylhexadecylether (Ex. 12) | ○ | ○ | ○ | ○ |
| | 1-methylpropyltetradecylether (Ex. 13) | ○ | ○ | ○ | ○ |
| | 1-methylpropyloctadecylether (Ex. 15) | ○ | ○ | ○ | ○ |
| | polyoxyethylene-1-methylpropyldodecylether (Ex. 22) | ○ | ○ | ○ | ○ |
| Comp. product | Light polyisobutene (Polysynlane (Nippon Fat and Oil Co.)) | ○ | ○ | ○ | Δ |
| | Squalane | ○ | ○ | Δ | X |
| | tri(2-ethylhexanoic acid)triglyceride (T.I.O (Nisshin Oil Mills) | ○ | ○ | X | X |
| | Isononyl isononanoate (Salacos 99 (Nisshin Oil Mills) | ○ | ○ | Δ | ○ |
| | Dioctylether | Δ | ○ | ○ | ○ |
| | Didodecylether | ○ | ○ | ○ | X solid at ordinary temperature |
| | 3-methylbutyltetradecylether | ○ | ○ | ○ | Δ |
| | 3-methylbutyloctadecylether | ○ | ○ | ○ | X solid at ordinary temperature |

As is apparent from Table 1, it was proved that the ether compounds of the present invention are odorless, do not change in color and odor with the elapse of time, have no stickiness and adequately low viscosity with good extendability.

Test Example 2

Removability of an oil type mascara and irritation when the oil type mascara is remove were evaluated for the ether compounds obtained in Examples 1, 3, 9, 10, 12, 13, 15 and 22 by the following method. A conventional general purpose oil solution, as control, was also evaluated in the same way. The results are shown in Table 2.

Evaluation Method (1) Removability of oil type mascara:

An oil type mascara of the following formulation was applied on a slide glass and left for 24 hours for drying. About 20 mg of the mascara was applied to an area of a circle of about 4 cm diameter on the slide glass. First, a slide glass having no mascara applied on it was placed on a white paper, and its color was measured ($E_0$) with a color difference meter, CR-300 (mfd. by MINOLTA). Then, the slide glass on which mascara was applied was placed, and the fouling by the mascara before cleaning was measured ($E_1$). Thereafter, 200 μl each of oil solutions (the ether compounds according to the present invention and the control general purpose lubricant) was applied to the mascara fouling, and massage was given 40 times to float the fouling, which was wiped off with a tissue paper. Finally, color was measured ($E_2$) at the place where the color was measured at first. The removal rate was calculated based on the following formula 1 using the color difference measured in this way.

$$\text{removal rate } (\%) = \left[1 - \frac{E_0 - E_2}{E_0 - E_1}\right] \times 100 \quad \text{[Formula 1]}$$

(2) Irritation to eyes:

| (Composition of oil type mascara) | |
|---|---|
| Carnauba wax | 7.0 (%) |
| Bees wax | 2.0 |
| Microcrystalline wax | 20.0 |
| Lanolin | 0.4 |
| Light liquid polyisobutene | 60.6 |
| Carbon black | 10.0 |
| Total | 100.0 |

The above oil type mascara was applied to eyelashes of five experts. After drying for 6 hour, the mascara was removed with absorbent cotton by massaging the eyes, whose eyelids were closed, with 0.5 g each of oil solutions (the ether compounds according to the present invention and the control general purpose lubricant) penetrated into the absorbent cotton. The irritation to eyes, while massaging, was evaluated by the following criterion.

No: All the five members felt no irritation

Yes: At least one members felt irritation

TABLE 2

|  |  | removing rate of oily mascara (%) | Stimulation to eye |
|---|---|---|---|
| Invention product | 1,3-dimethylbutyldodecylether (Ex. 1) | 99 or more | none |
|  | 1,3-dimethylbutyltetradecylether (Ex. 3) | 95 | none |
|  | 1,3-dimethylbutylhexadecy1ether (Ex. 9) | 83 | none |
|  | 1,3-dimethlbutyloctadecylether (Ex. 10) | 80 | none |
|  | isopropylhxadecylether (Ex. 12) | 99 or more | none |
|  | 1-methylpropyltetradecylether (Ex. 13) | 99 or more | none |
|  | 1-methylpropyloctadecylether (Ex. 15) | 86 | none |
|  | polyoxyethylene-1-methylpropyldodecylether (Ex. 22) | 80 | none |
| Comp. product | Tri(2-ethylhexanoic acid)triglyceride | 25 | none |
|  | Dicaprinic acid neopentylglycol | 10 | none |
|  | Squalane | 5 | none |
|  | Dioctylether | 99 or more | yes |
|  | 1,3-dimethylbutyloctylether | 99 or more | yes |

As is apparent from Table 2, it is revealed that the asymmetrical ether compounds of the present invention have superior oil removability of oil type mascara and give no sense of stimulation to human eyes.

Example 28

Cleansing oils having composition shown in Tables 3 and 4 were prepared by a conventional method. The cleansing oils produced was evaluated by the method shown hereunder, for the removability, detergency, irritation to human eyes, feeling when applied, and emulsification property. The results are shown in Tables 3 and 4.

The oil type mascara whose formulation was shown in below, was used as the typical fouling for the purpose of evaluating cleansing oils.

| (Composition of oil type mascara) | |
|---|---|
| Carnauba wax | 7.0 (%) |
| Bees wax | 2.0 |
| Microcrystalline wax | 20.0 |

| -continued | |
|---|---|
| (Composition of oil type mascara) | |
| Lanolin | 0.4 |
| Light liquid polyisobutene | 60.6 |
| Carbon black | 10.0 |
| Total | 100.0 |

TABLE 3

| Component | Invention product | | | | | | | | |
|---|---|---|---|---|---|---|---|---|---|
| (%) | (1) | (2) | (3) | (4) | (5) | (6) | (7) | (8) | (9) |
| Decyl 1,1,3,3-tetramethylbutylether | 80 | | | | | | | | |
| Dodecyl 1,3-diethylbutylether | | 80 | | | | | | | |
| Dodecyl 1,1,3,3-tetramethylbutylether | | | 80 | | | | | | |
| Dodecyl 1-(1-methylethyl)-2-methylpropylether | | | | 80 | | | 60 | | |
| Myristyl 1,3-dimethylbutylether | | | | | 80 | | | | |
| Dodecyl 3,5,5-trimethylhexylether | | | | | | 80 | | | |
| Palmityl 1,3-eimethylbutylether | | | | | | | 80 | | |
| Isostearyl 1,3-dimethylbutylether*1 | | | | | | | | 20 | |
| Myristyl 1,3-dimethylbutylether | | | | | | | | | 80 |
| Polyoxyethylene(20)glyceryltriisostearate*2 | 20 | 20 | 20 | 20 | 20 | 20 | 20 | 20 | |
| Total | 100 | 100 | 100 | 100 | 100 | 100 | 100 | 100 | 100 |
| Detergency rate (%) | 91 | 92 | 92 | 87 | 84 | 84 | 86 | 91 | 90 |
| Detergency | ◯ | ◯ | ◯ | ◯ | ◯ | ◯ | ◯ | ◯ | ◯ |
| Stimulation to the Eye | ◯ | ◯ | ◯ | ◯ | ◯ | ◯ | ◯ | ◯ | ◯ |
| Feelin of Use | ◯ | ◯ | ◯ | ◯ | ◯ | ◯ | ◯ | ◯ | ◯ |
| Emulsifying ability | ◯ | ◯ | ◯ | ◯ | ◯ | ◯ | ◯ | ◯ | ◯ |

*1 synthesized by Emery type isostearyl alcohol as a raw material
*2 EMALEX GWIS 320 (mfd. by Nippon Emulsion Co., Ltd.)

TABLE 4

| Component | Comparative product | | | |
|---|---|---|---|---|
| (%) | (1) | (2) | (3) | (4) |
| Light polyisobutene*3 | 80 | | | |
| Tri(2-ethylhexanoic acid) triglyceride*4 | | 80 | | |
| Isononane acid isononyl*5 | | | 80 | |
| Cyclic silicone (tetramer)*6 | | | | 80 |

TABLE 4-continued

| Component (%) | Comparative product | | | |
|---|---|---|---|---|
| | (1) | (2) | (3) | (4) |
| Polyoxyethylene(20)glyceryltriisostearate*[2] | 20 | 20 | 20 | 20 |
| Total | 100 | 100 | 100 | 100 |
| Detergency rate (%) | 21 | 25 | 79 | 75 |
| Detergency | X | X | ◯ | ◯ |
| Stimulation to the Eye | ◯ | ◯ | X | ◯ |
| Feelin of Use | X | X | X | ◯ |
| Emulsifying ability | ◯ | ◯ | ◯ | X |

*[3]Polysynlane (mfd. by Nippon Fat and Oil)
*[4]T.I.O (mfd. by Nisshin Oil Mills)
*[5]Salacos 99 (mfd. by Nisshin Oil Mills)
*[6]SILICONE SH-244 (mfd. by Toray-Dow Corning-Silicone)

Evaluation Method (1) Removability:

The above oil type mascara was applied on a slide glass and left for 24 hours for drying. About 20 mg of the mascara was applied to an area of a circle of about 4 cm diameter on the slide glass. First, a slide glass having no mascara applied on it was placed on a white paper, and its color was measured ($E_0$) with a color difference meter, CR-300 (manufactured by MINOLTA). Then, the slide glass on which mascara was applied was placed, and the fouling by the mascara before cleaning was measured ($E_1$). Thereafter, 200 μl of the cleansing oil was applied to the mascara fouling, and massage was given 40 times to float the fouling, which was wiped off with a tissue paper. Finally, color was measured ($E_2$) at the place where the color was measured at first. The removal rate was calculated based on the formula mentioned before using the color difference measured in this way.

(2) Detergency:

The above oil type mascara was applied to eyelashes of five experts. After drying for 6 hour, the mascara was removed with absorbent cotton by massaging the eyes, whose eyelids were closed, with each 0.5 g of the samples penetrated into the absorbent cotton. The detergency was evaluated visually by the following criterion. What gets 1.2 or more as the average point of the 5 members' evaluation is rated as good (◯); what gets less than 1.2 is rated as poor (x).

Cleaned well: 2 points
Cleansed fairly: 1 point
Cleansed hardly: 0 point (3) Irritation to eyes:

Irritation to eyes, when massaged during the detergency evaluation, was also evaluated.

The cleansing oil with no irritation felt by all the five members, was rated as good (◯). Cleansing oil with irritation felt by even one member was rated as poor (x).

(4) Feeling when applied:

Feeling (stickiness) when and after applied in the detergency evaluation, was evaluated based by the following criterion. What gets 1.4 or more as the average point of the 5 members' evaluation is rated as good (◯); what gets less than 1.4 is rated as poor (x).

Not sticky: 2 points
Slightly sticky: 1 point
Sticky: 0 point.

(5) Emulsification Property:

The cleansing oil was added by water in twice amount of the cleansing oil. Emulsification property was evaluated visually by the following criterion.

Emulsified (uniform white turbidity): ◯
not emulsified (separation): x

Example 29

A water-washable cleansing oil of the below composition was prepared by a conventional method.

The cleansing oil obtained was applied on the face. No irritation to eyes was felt while applied and water-washed. Lipstick, foundation and oil type mascara were nearly completely removed. Furthermore, no uncomfortable stickiness was experienced after use.

| (Components) | (%) |
|---|---|
| Myristyl 1,3-dimethylbutyl ether | 60 |
| Isopropyl palmitate | 18 |
| Dimethyl polysiloxane *[7] | 2 |
| Polyoxyethylene(20) glyceryl triisostearate *[2] | 18 |
| polyoxyethylene(30) glyceryl triisostearate *[8] | 2 |
| Total | 100 |

*[7]: SILICONE KF96A (6 cs) (mfd. by SHIN-ETSU SILICONE)
*[8]: EMULEX GWIS 330 (manufactured by NIPPON EMULSION)

Example 30

A water-washable cleansing cream of the below composition was prepared by a conventional method. The cleansing cream produced was used on the face with make-up. No irritation to eyes was felt while applied and water-washed. Lipstick, foundation and oil type mascara were nearly completely removed. Furthermore, no uncomfortable stickiness was experienced after use.

| (Components) | (%) |
|---|---|
| Myristyl 1,3-dimethylbutyl ether | 35.0 |
| Isotridecyl myristate | 10.0 |
| Tri(2-ethyl hexoate) triglyceride*[4] | 5.0 |
| Polyoxyethylene(10) glyceryl triisostearate*[9] | 1.5 |
| Polyoxyethylene(30) glyceryl triisostearate*[8] | 4.0 |
| Polyoxyethylene(20) monostearate*[10] | 0.5 |
| Methylparaben | 0.1 |
| Glycerine | 4.0 |
| Polyethylene glycol 6000 | 2.0 |
| Polyethylene glycol 8360 monostearate | 1.2 |
| Perfume | 0.2 |
| water | balance |
| Total | 100 |

*[9]: EMULEX GWIS 310 (mfd. by NIPPON EMULSION)
*[10]: REODOL SUPER TWS-120 (mfd. by KAO)

Example 31

A cleansing lotion with the formulation shown below was prepared by a conventional method.

The cleansing lotion obtained was applied on the face with cosmetics. No irritation to eyes was felt while applied and water-washed. Lipstick, foundation and oil type mascara were nearly completely removed. Furthermore, no uncomfortable stickiness was experienced after use.

| (Components) | (%) |
|---|---|
| Palmityl 1,3-dimethylbutyl ether | 30.0 |
| Light isopolybutene*[3] | 5.0 |

31

-continued

| (Components) | (%) |
|---|---|
| Tri(2-ethyl hexoate) triglyceride*[4] | 5.0 |
| Polyoxyethylene(10) glyceryl triisostearate*[9] | 0.5 |
| Polyoxyethylene(40) hardened castor oil triisotearate*[11] | 0.1 |
| Methylparaben | 0.1 |
| Perfume | 0.3 |
| water | balance |
| Total | 100 |

*[11]: EMULEX RWIS 340 (mfd. by NIPPON EMULSION)

Example 32

A cleansing gel with the formulation shown below was prepared by a conventional method.

The cleansing gel obtained was applied on the face with make-up. No irritation to eyes was felt while applied and water-washed. Lipstick, foundation and oil type mascara were nearly completely removed. Furthermore, no uncomfortable stickiness was experienced after use.

| (Components) | (%) |
|---|---|
| Myristyl 1,3-dimethylbutyl ether | 60.0 |
| Polyoxyethylene(40) glyceryl triisostearate*[12] | 12.0 |
| Glycerin | 15.0 |
| Methylparaben | 0.1 |
| Perfume | 0.3 |
| water | balance |
| Total | 100 |

*[12]: EMULEX GWIS 340 (mfd. by NIPPON EMULSION)

Example 33

A wipe-off type cleansing oil having the composition shown below was prepared by a conventional method.

The cleansing oil obtained was applied on the face with make-up. No irritation to eyes was felt while applied and water-washed. Lipstick, foundation and oil type mascara were nearly completely removed. Furthermore, no uncomfortable stickiness was experienced after use.

| (Components) | (%) |
|---|---|
| Palmityl 1,3-dimethylbutyl ether | 50.0 |
| Isopropyl myristate | 20.0 |
| Cyclic silicone (tetramer)*[6] | 25.0 |
| Dimethyl polysiloxane*[7] | 5.0 |
| Total | 100 |

We claim:

1. An ether compound having the formula (I):

$$R^1-O-(AO)_n-R^2 \quad (I)$$

wherein $R^1$ is an α-branched alkyl group bearing an α-hydrogen atom, $R^2$ is an alkyl or alkenyl each being either branched or straight chain, each having 10 to 30 carbon atoms, A is an alkylene having 2 to 12 carbon atoms, n is an integer from 0 to 30, A's being the same as or different form one another.

2. The ether compound of claim 1, wherein $R^1$ is selected from the group consisting of:

$CH_3-CH(CH_3)-CH_2-CH(CH_3)-$, $CH_3-CH_2-CH(CH_3)-$, $CH_3-CH(CH_3)-CH_2-CH(CH_2-CH(CH_3)_2)-$, $CH_3-CH_2-CH_2-CH_2-CH_2-CH_2-CH(CH_3)-$, or an alkyl group having two or more side chains.

3. The compound as claimed in claim 1, in which $R^1$ is selected from $CH_3-CH(CH_3)-CH_2CH(CH_3)-$, $CH_3-CH(CH_3)CH_2CH_2CH_2CH(CH_3)CH_2CH_2-$ and $CH_3-CH(CH_3)-CH_2-CH\{CH_2-CH(CH_3)_2\}-$.

4. The compound as claimed in claim 1 in which A is an ethylene group.

5. The compound as claimed in claim 1, which is represented by the following formula (II):

$$CH_3-CH(CH_3)-CH_2-CH(CH_3)-O-(EO)_n-R^5 \quad (II)$$

wherein $R^5$ is a straight or branched alkyl group having 10 to 22 carbon atoms, E is an ethylene group and n is the same as defined in claim 1.

6. A process for producing the ether compound as defined in claim 1, which comprises reacting a carbonyl compound represented by the following formula (III):

$$\begin{array}{c} R^3 \\ \phantom{R}\diagdown \\ \phantom{RRR}C=O \\ \phantom{R}\diagup \\ R^4 \end{array} \quad (III)$$

(wherein $R^3$ and $R^4$ are the same or different from each other satisfying that $$R^3-\underset{|}{C}H-R^4$$

corresponds with the $R^1$ as defined in claim 1) with a hydroxy compound represented by the following formula (IV):

$$HO-(AO)_n-R^2 \quad (IV)$$

(wherein $R^2$, n and A are the same as defined in claim 1) in a hydrogen gas atmosphere in the presence of a palladium catalyst supported on carbon powder.

7. The process as claimed in claim 6 in which $R^3$ represents a methyl group and $R^4$ is a group selected from $CH_3-CH(CH_3)CH_2-$, $CH_3-CH_2-$, $CH_3CH_2CH_2CH_2CH_2CH_2-$.

8. The process as claimed in claim 6, in which a pH of the palladium catalyst, defined in an aqueous solution comprising 30 g of ion exchanged water and 2 g of the catalyst powder dispersed, is in the range of 1 to 8.

9. The process claimed in claim 6, in which the carbonyl compound represented by the formula (III) and the hydroxyl compound represented by the formula (IV) are reacted at a molar ratio of (III):(IV)=1:1 to 20:1.

10. The process as claimed of claim 6, in which the reaction is carried out in a hydrogen gas pressure of 1 to 250 kg/cm².

11. A method of removing make-up comprising:

i) applying to a surface having make-up thereon, a cosmetic composition comprising an ether compound having the formula (I):

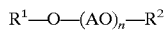

(I)

wherein
$R^1$ is an α-branched alkyl group bearing an α-hydrogen atom,
$R^2$ is an alkyl or alkenyl each being either branched or straight chain, each having 10 to 30 carbon atoms,
A is an alkylene having 2 to 12 carbon atoms,
n is an integer from 0 to 30,
A's being the same as or different form one another; and ii) removing said cosmetic composition.

12. A make-up cosmetics removing agent composition which comprises: an ether compound having the formula (I):

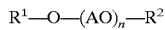

(I)

wherein $R^1$ is an α-branched alkyl group bearing an α-hydrogen atom,
$R^2$ is an alkyl or alkenyl each being either branched or straight chain, each having 10 to 30 carbon atoms,
A is an alkylene having 2 to 12 carbon atoms,
n is an integer from 0 to 30,
A's being the same as or different form one another.

13. The composition as claimed in claim 12, in which the amount of the ether compound is in the range of 6 to 95 wt. %.

14. A method of removing cosmetics from skin, comprising applying an effective amount of the ether compound as defined in claim 1 to skin having a cosmetic applied thereon.

* * * * *